United States Patent
Caudillo et al.

[11] Patent Number: 5,823,342
[45] Date of Patent: Oct. 20, 1998

[54] PACKAGING FOR MITRAL OR AORTIC HEART VALVE DEVICE

[75] Inventors: Roberto Caudillo; Tammi Klostermeyer, both of Austin, Tex.

[73] Assignee: Sulzer Carbomedics Inc., Austin, Tex.

[21] Appl. No.: 970,227

[22] Filed: Nov. 14, 1997

[51] Int. Cl.[6] .......................... A61B 17/06; B65D 85/30; A61F 2/24
[52] U.S. Cl. ................................ 206/438; 206/363; 623/2
[58] Field of Search ................................... 206/363, 438, 206/583; 623/2

[56] References Cited

U.S. PATENT DOCUMENTS

| | | | |
|---|---|---|---|
| 4,101,031 | 7/1978 | Cromie | 206/438 |
| 4,512,471 | 4/1985 | Kaster et al. | 206/438 |
| 5,560,487 | 10/1996 | Starr | 206/438 |

Primary Examiner—Bryon P. Gehman
Attorney, Agent, or Firm—Kenneth S. Barrow

[57] ABSTRACT

Packaging (10) for a heart valve device (11) is disclosed that includes a container (42) having an inner compartment. The container (42) has an aortic orientation and a mitral orientation and is constructed to be opened in either orientation. The packaging (10) also includes an aortic support member (22, 24, 26), located in the compartment, that supports the heart valve device (28) when the container (42) is opened in the aortic orientation. The heart valve device (11) is supported such that it is prepared for receiving a holding instrument for implantation as an aortic valve. The packaging (10) further includes a mitral support member (20), located in the compartment, that supports the heart valve device (11) when the container (42) is opened in the mitral orientation. The heart valve device (11) is supported such that it is prepared for receiving a holding instrument for implantation as a mitral valve.

14 Claims, 5 Drawing Sheets

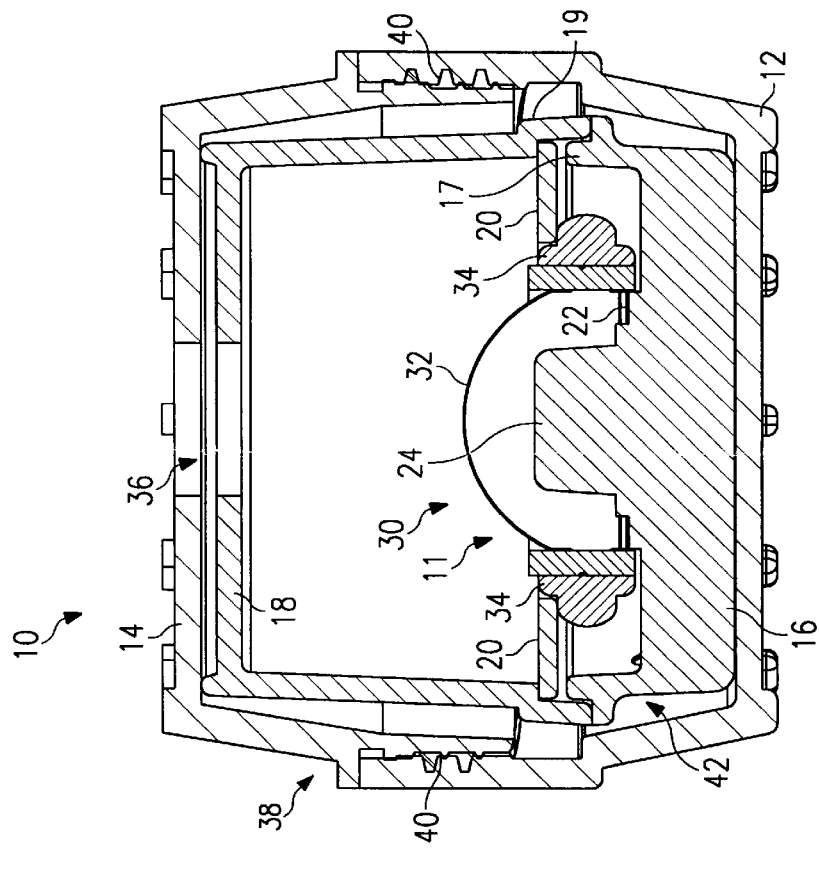
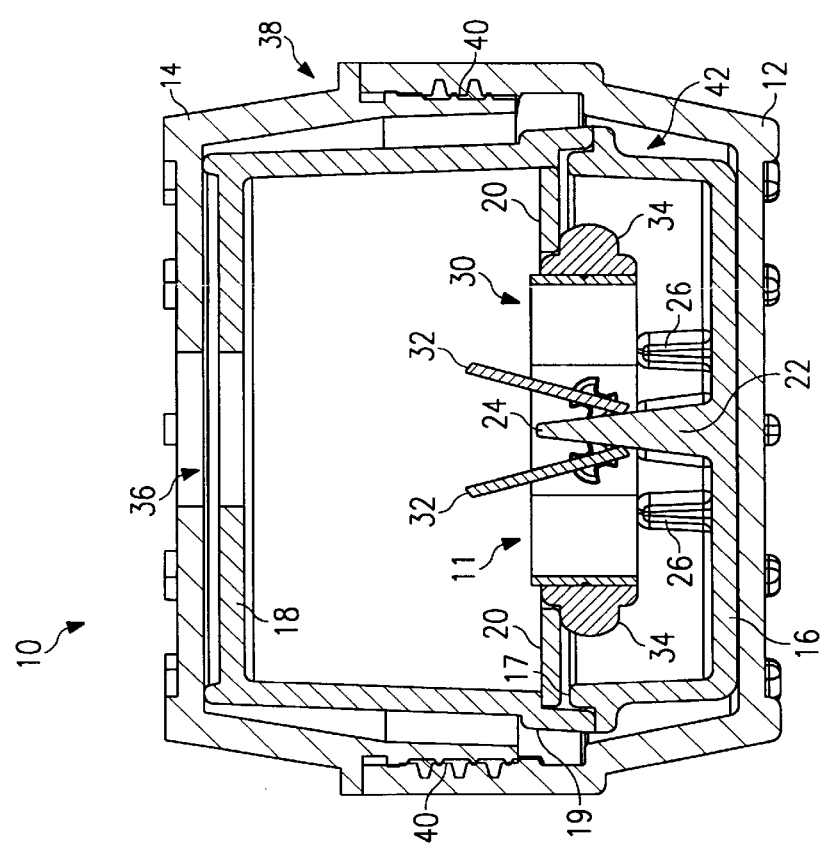

PACKAGING FOR MITRAL OR AORTIC HEART VALVE DEVICE

TECHNICAL FIELD OF THE INVENTION

The present invention relates in general to the field of packaging for implant devices, and more particularly to packaging for a heart valve device.

BACKGROUND OF THE INVENTION

There are a number of conventional types of packaging for aortic and mitral heart valve implant devices. Initially, heart valve devices were simply packaged in a pouch. The surgical personnel could then remove the heart valve device from the pouch, hold the device in one hand, and use the other hand to grab the device with a holding instrument. The holding device could then be used to position the heart valve device for implantation. Typically, the heart valve device can be implanted as either an aortic valve or a mitral valve, so it is critical that the surgical personnel correctly orient the device. Understandably, the pouch packaging method is subject to numerous problems, an important one of which is the implantation of heart valve devices in the wrong orientation by mistake.

A second packaging method is to package the heart valve device in such a way that the device is oriented one way by the packaging. Thus, when packaging for an aortic heart valve device is opened, the device is positioned for an aortic implant (i.e., leaflets extending upward). Conversely, when packaging for a mitral heart valve device is opened, the device is positioned for a mitral implant (i.e., leaflets extending downward). In this manner, the surgical personnel is encouraged to pick up the device from the packaging in the correct orientation. However, mistakes might still occur, in part, because surgical personnel lose track of the correct orientation once the device is in their hand. In addition, because each package is dedicated to one orientation, a medical facility, such as a hospital or surgical clinic, would need to stock a full range of both mitral and aortic heart valve devices.

Another conventional packaging method precludes a mistake in orientation by pre-attaching a head of a holding instrument to the heart valve device. The heart valve device is then picked up by attaching the handle of the holding instrument to the head. This insures the correct orientation of the heart valve device for implantation. However, because the head is pre-attached to the device, each device is intended to be a mitral valve or is intended to be an aortic valve replacement. Similar to the previous packaging method, the pre-attached head method generates a need for a medical facility to stock a full range of both aortic and mitral devices.

It is therefore desirable to provide packaging for heart valve devices that helps to insure proper implant orientation while also reducing the inventory requirements for medical facilities.

SUMMARY OF THE INVENTION

In accordance with the present invention, packaging for a heart valve device is disclosed that provides advantages over conventional heart valve device packaging.

According to one aspect of the present invention, the packaging includes a container that has an inner compartment. The container has an aortic orientation and a mitral orientation and is constructed to be opened in either orientation. An aortic support member, located in the compartment, supports the heart valve device when the container is opened in the aortic orientation such that the device is prepared for receiving a holding instrument for implantation as an aortic valve. The packaging also includes a mitral support member, located in the compartment, that supports the heart valve device when the container is opened in the mitral orientation such that the device is prepared for receiving a holding instrument for implantation as a mitral valve.

More specifically, the aortic support member can support the heart valve device with the leaflets of the heart valve device held in an open position. In particular, the leaflets can be held open by a tab extending from a ridge that provides central support for the heart valve device. Further, a pair of additional ridges can provide lateral support for the heart valve device.

In one embodiment, the container can comprise two container portions, formed to removably engage one another, to which the aortic support member and the mitral support member are respectively coupled. In particular, the aortic support member can be formed integral with one container portion, and the mitral support member can be a shelf member removably located inside the other container portion.

A technical advantage of the present invention is that the packaging allows a heart valve device to be packaged in one configuration and be used for either aortic or mitral valve replacements depending in which orientation the packaging is opened.

Another technical advantage of the present invention is that the packaging encourages proper orientation by preparing the heart valve to receive a holding instrument while the device is still supported in the proper orientation by the packaging. Further, the heart valve device can be picked up in either the aortic or mitral orientation without the surgical personal touching the heart valve device itself. In contrast, conventional packaging is designed to be used for only one type of valve implant (e.g., aortic or mitral) or does not prepare the devices to be ready to receive a holding instrument.

A further technical advantage of the present invention is a reduction in the need for expensive duplicate inventory of both aortic and mitral heart valve devices. Further, the shelf space required to stock a full line of heart valve devices is reduced as well. A medical facility, which may have a low budget and minimal shelf space, can maintain stock of a complete line of aortic and mitral valve devices with one set of devices that can be used for either orientation.

Additional technical advantages should be readily apparent to one skilled in the art from the drawings, description, and claims.

BRIEF DESCRIPTION OF THE DRAWINGS

A more complete understanding of the present invention and advantages thereof may be acquired by referring to the following description, taken in conjunction with the accompanying drawings, in which like reference numbers indicate like features and wherein:

FIGS. 2A and 2B are cross-section views of the packaging of FIG. 1 after assembly;

DETAILED DESCRIPTION OF THE INVENTION

Figure 1:
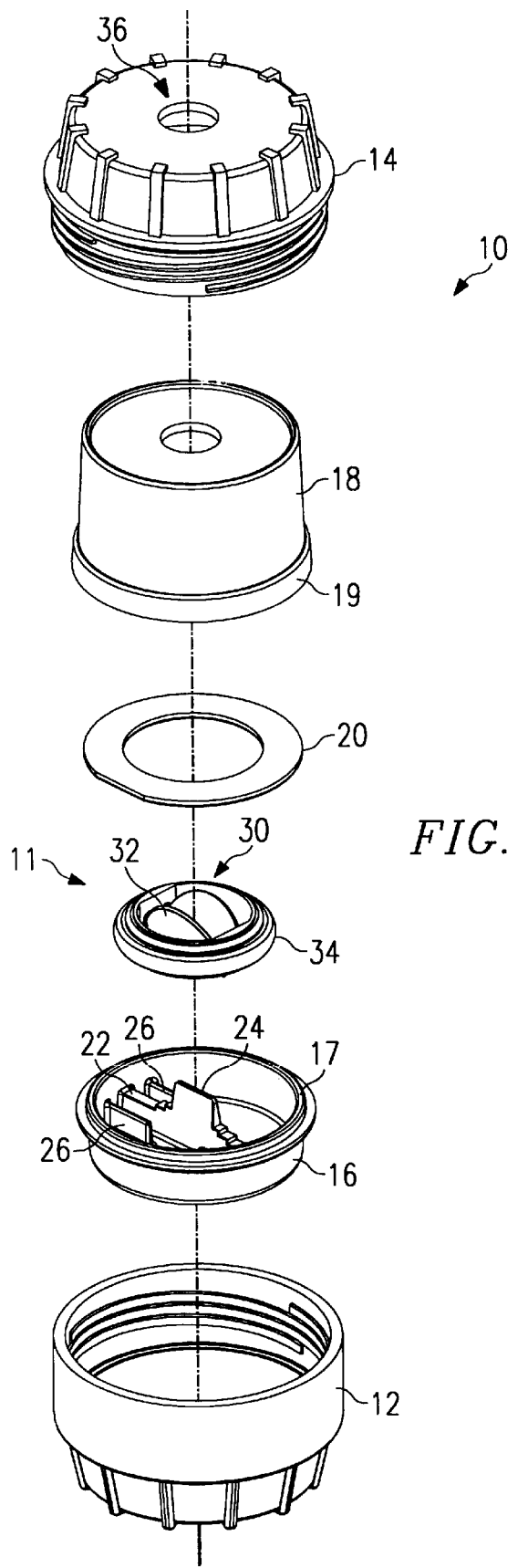
FIG. 1 is an explosion view of one embodiment of packaging for a heart valve device in an aortic orientation according to the teachings of the present invention.

FIG. 1 is an explosion view of one embodiment of packaging for a heart valve device, indicated generally at 10, in an aortic orientation according to the teachings of the present invention. In the illustrated embodiment, packaging 10 comprises an outer shell having a first portion 12 and a second portion 14. Outer shell portion 12 and outer shell portion 14 are formed to removably engage one another. In particular, outer shell portion 14 and outer shell portion 12 can be formed with threads such that the two can be screwed together.

In the illustrated embodiment, the outer shell forms a housing for a container that has a first container portion 16 and a second container portion 18. Container portion 16 and container portion 18 are formed to removably engage one another. In particular, container portion 16 has a perimeter ridge 17 sized to fit inside a perimeter rim 19 of container portion 19. Container portion 16 and container portion 18, when engaged, have inner surfaces that define an inner compartment for packaging a heart valve device, indicate generally at 11.

In the embodiment of FIG. 1, container portion 18 provides a base for a mitral support member that comprises a shelf 20. Shelf 20 is sized to fit inside and removably engage (e.g., press fit) rim 19 of container portion 18. Shelf 20 provides a support for heart valve device 11 when container portion 18 is on bottom (e.g., as shown in FIGS. 3, 4A, 4B, and 5). Other implementations are also possible, for example, where the mitral support member is formed integral with container portion 18. Also in the embodiment of FIG. 1, container portion 16 provides a base for an aortic support member that comprises a central ridge 22 and a pair of lateral ridges 26. As shown, central ridge 22 and lateral ridges 26 can be coupled to and formed integral with the inner surface of container portion 16. Further, central ridge 22 can include a tab 24 that extends into the inner compartment formed when container portions 16 and 18 are engaged. When container portion 16 is on bottom, central ridge 22 provides central support and lateral ridges 26 provide lateral support for heart valve device 11. In this embodiment, central ridge 22 and lateral ridges 24 are formed integral with container portion 16. However, other implementations are also possible, for example, where the aortic support member is a separate component from container portion 16.

Heart valve device 11 typically comprises an orifice 30 in which leaflets 32 are positioned and allowed to rotate. Heart valve device 11 also comprises a sewing cuff 34 which is used to affix the heart valve device 11 to the patient's heart. Heart valve device 11 can operate as a mitral or aortic heart valve when implanted in a human heart depending upon its orientation when implanted. To insure that heart valve device 11 can be sterilized, a hole 36 is provided in packaging 10 to allow sterilization of the inside of package 10. Also, in the illustrated embodiment, except for shelf 20, none of the components of packaging 10 are size dependent depending upon the size of heart valve device 11. Thus packaging 10 is easy to manufacture and assemble because most of the components are standard across the heart valve device product line.

According to the present invention, the container formed by container portions 16 and 18 has an aortic orientation and a mitral orientation. When in the aortic orientation, container portion 16 is on bottom, and heart valve device 11 is supported by the aortic support member formed by central ridge 22 and lateral ridges 26. Central ridge 22 supports heart valve device 11 substantially in the center while lateral ridges 26 support heart valve device 11 to keep it from rocking on central ridge 22. Further, in this orientation, leaflets 32, which otherwise would fall to close off orifice 30, can be held open by tab 24 which extends between the leaflets.

After the outer shell of packaging 10 is opened, the inner container can be removed and positioned in the aortic or mitral orientation. In the aortic orientation, container portion 16 is positioned at the bottom with container portion 18 on top. Container portion 18 can then be removed along with shelf 20. This leaves heart valve device 11 supported by the aortic support member formed by central ridge 22 and lateral ridges 26 with leaflets 32 are held open by tab 24. A holding instrument can then be used to extract heart valve device 11 and hold it for implantation in a surgical procedure. Tab 24 holds leaflets 32 open to ensure that the holding instrument can be used without having to manually manipulate leaflets 32. Thus, in the aortic orientation, the heart valve device 11 is supported such that it is prepared for receiving a holding instrument for implantation as an aortic valve.

In one embodiment, packaging 10 is labeled to indicate the aortic and mitral orientations. If opened in one orientation, leaflets 32 are held open, and heart valve device 11 is ready to be picked up with a holding instrument and implanted in the aortic position. If the package is opened in the opposite orientation, leaflets 32 remain open by operation of gravity, and heart valve device 11 is ready to be picked up with a holding device and implanted in the mitral position.

According to the present invention, packaging 10 allows heart valve device 11 to be packaged in one configuration and be used for either aortic or mitral valve replacements depending in which orientation packaging 10 is opened. Packaging 10 thus encourages proper orientation by preparing heart valve device 11 to receive a holding instrument while the device is still supported in the proper orientation by packaging 10. Further, heart valve device 11 can be picked up without surgical personnel touching heart valve device 11. In contrast, conventional packaging is designed to be used for only one type of valve implant (e.g., aortic or mitral) or does not prepare the devices to be ready to receive a holding instrument. Further, by using packaging 10, the need for expensive duplicate inventory of both aortic and mitral heart valve devices is reduced along with the shelf space required to stock a full line of heart valve devices. The present invention allows a medical facility, which may have a low budget and minimal shelf space, can maintain stock of a complete line of aortic and mitral valve devices with one set of devices that can be used for either orientation.

FIGS. 2A and 2B are cross-section views of packaging 10 of FIG. 1 after assembly. As shown, an outer shell, indicated generally at 38, is formed by the engaging of outer shell portion 12 and outer shell portion 14 using threads 40. A container 42 is housed inside outer shell 38 and is formed by container portion 16 and container portion 18. In this embodiment, as shown, ridge 17 of container portion 16 fits inside rim 19 of container portion 18. In the aortic orientation of FIGS. 2A and 2B, heart valve device 11 rests on central ridge 22 and lateral ridges 26 with leaflets 32 held open by tab 24. As can be seen from FIG. 2A, space in orifice 30 is provided for receiving a holding device due to tab 24 holding leaflets 32 in an open position. If not for tab 24, leaflets 32 would fall to the closed position and obstruct orifice 30. After outer shell portions 12 and 14, container portion 18, and shelf 20 are removed, heart valve device 11 can be picked up for implantation in the aortic position as an aortic valve replacement.

Figure 3:
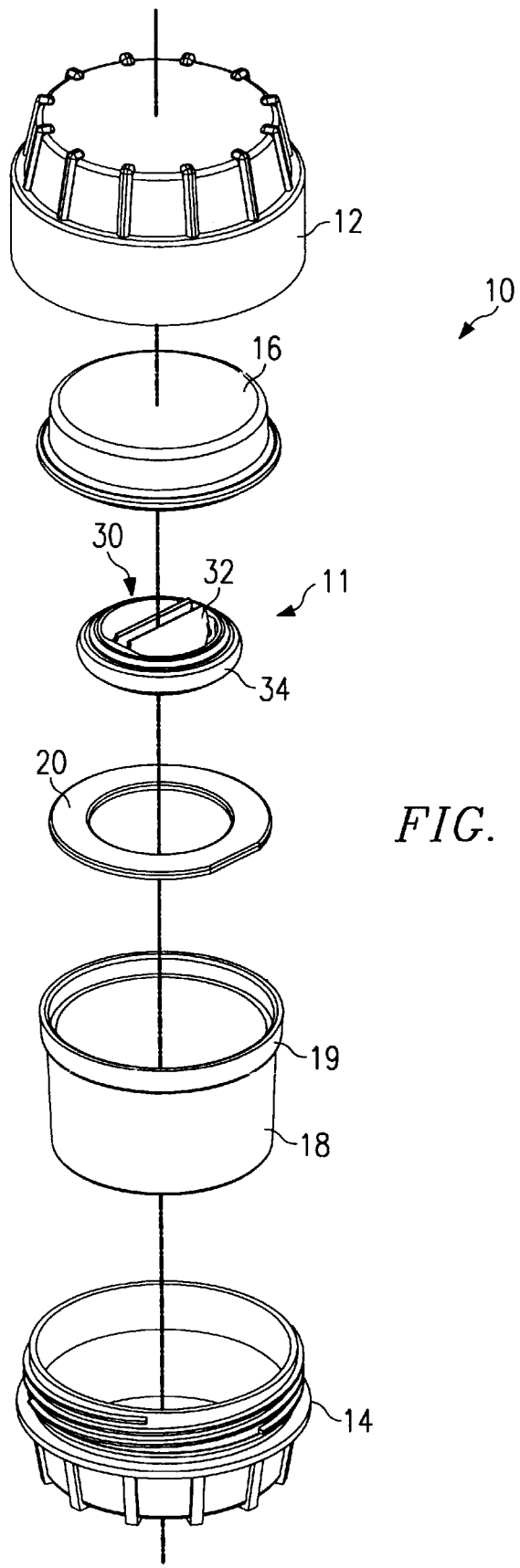
FIG. 3 is an explosion view of the packaging of FIG. 1 in the mitral orientation according to the present invention.

FIG. 3 is an explosion view of packaging 10 in the mitral orientation. As shown, outer shell portion 14 is now oriented at the bottom of packaging 10 and outer shell portion 12 is at the top. Similarly, container portion 18 is oriented at the bottom, and container portion 16 is oriented at the top. Shelf 20 fits inside rim 19 of container portion 18 and supports heart valve device 11 by sewing cuff 34. Due to gravity, leaflets 32 naturally fall to an open position thus allowing space within orifice 30 to receive a holding instrument. Thus, in the mitral orientation, heart valve device 11 is prepared to receive a holding instrument for implantation as a mitral valve.

Figure 4:
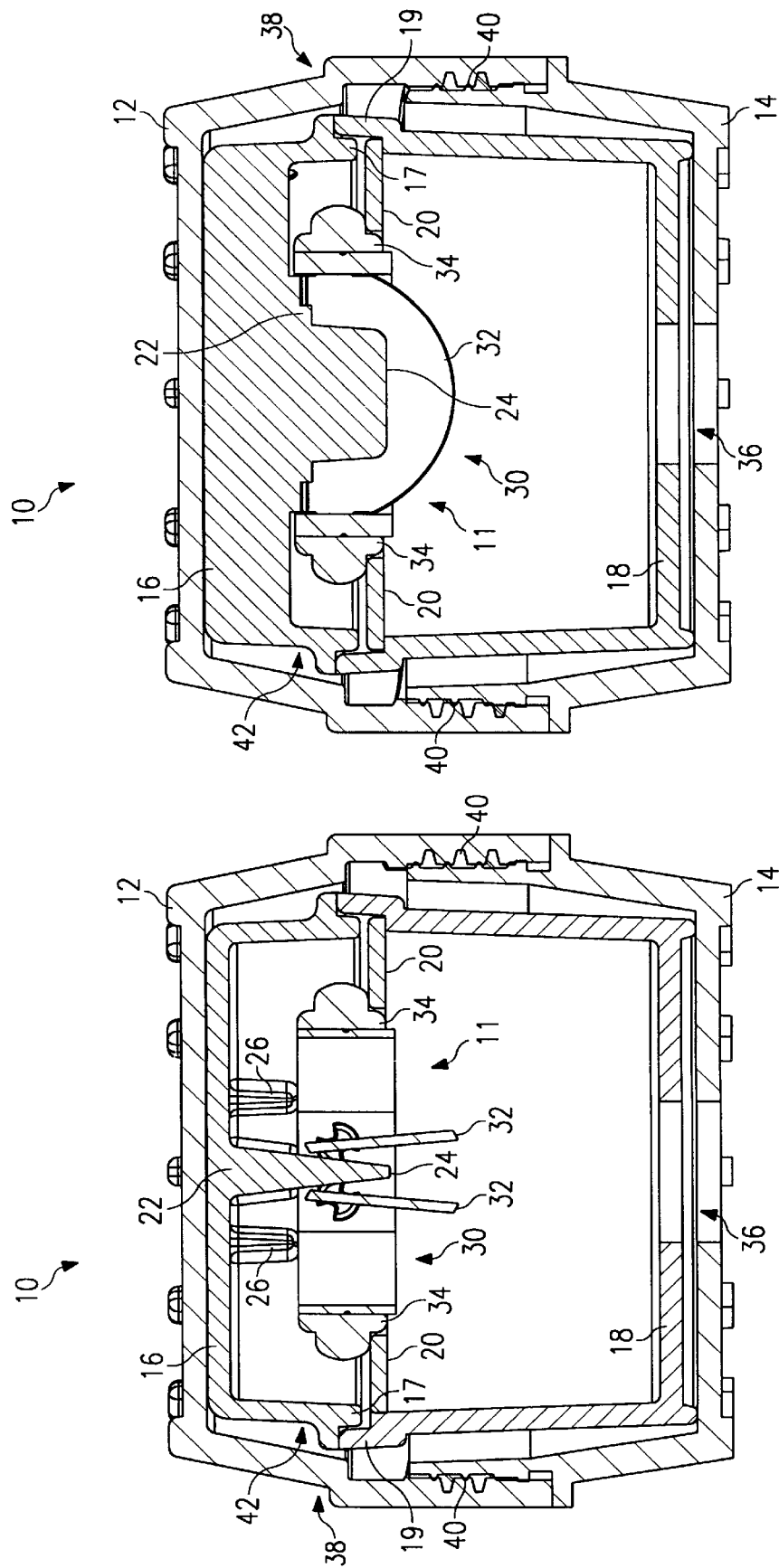
FIGS. 4A and 4B are cross-section views of the heart valve packaging assembly of FIG. 3 after assembly.

FIGS. 4A and 4B are cross-section views of packaging assembly 10 of FIG. 3 after assembly. As shown, outer shell 38 is now positioned with outer shell portion 14 on bottom, and container 42 is positioned with container portion 18 on bottom. In this mitral orientation, sewing cuff 34 of heart valve device 11 is supported by shelf 20 which, in turn, is supported by container portion 18. In this position, leaflets 32 naturally fall to the open position leaving space within orifice 30 for receiving a holding instrument. After outer shell portions 12 and 14 and container portion 16 are removed, heart valve device 11 can be picked up for implantation in the mitral position for a mitral valve replacement.

Figure 5:
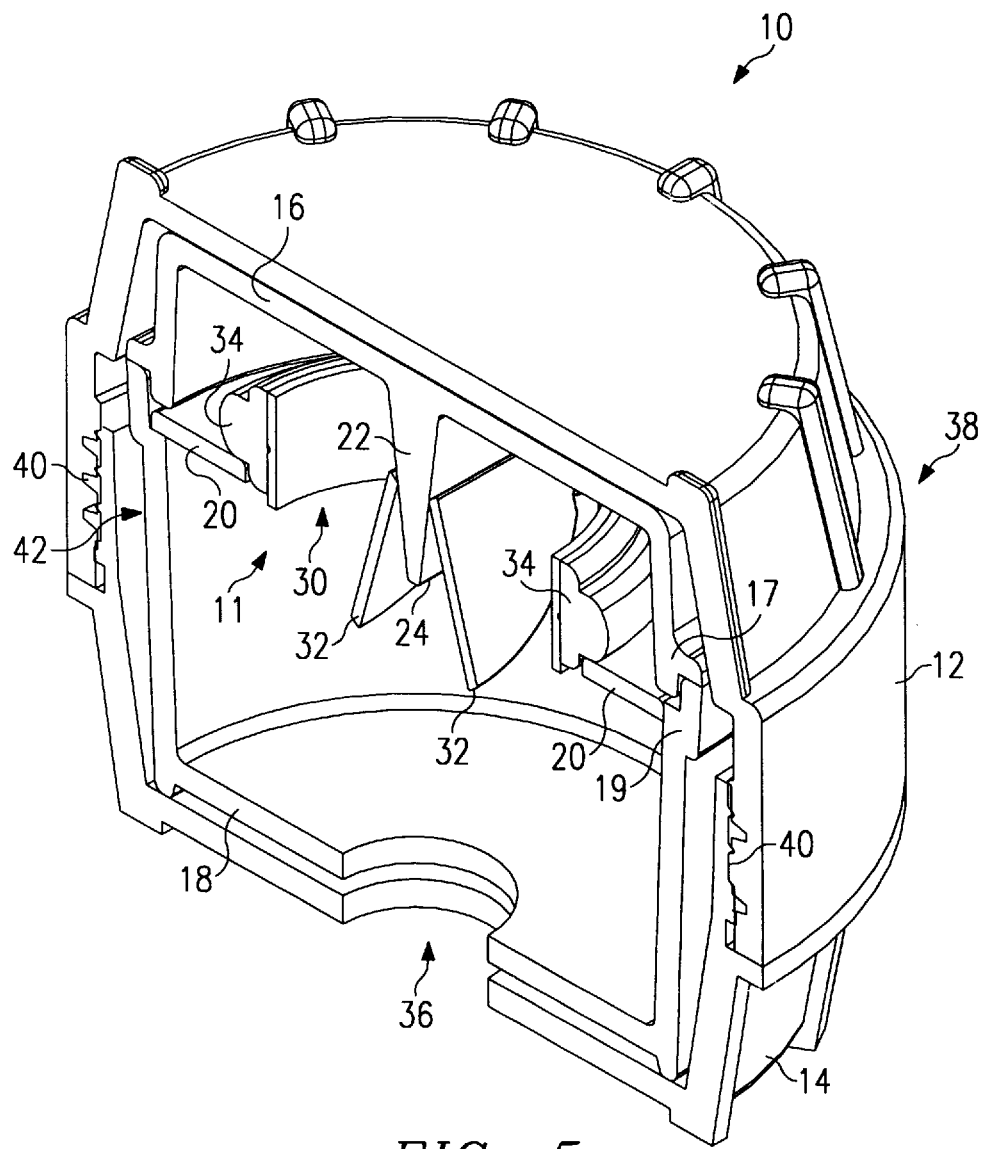
FIG. 5 is a cut-away perspective view of the packaging of FIG. 3 after assembly.

FIG. 5 is a cut-away perspective view of packaging 10 of FIG. 3 after assembly. As shown, in the mitral orientation, leaflets 32 of heart valve device 11 drop open such that heart valve device 11 is prepared for receiving a holding instrument for mitral implantation. It can also be seen that, if packaging assembly 10 were oppositely positioned in the aortic orientation, heart valve device 11 would be supported with leaflets 32 held open by tab 24 such that heart valve device 11 is prepared for a holding instrument for aortic implantation.

According to the present invention, the packaging for a heart valve device allows the same heart valve device to be used for either an aortic or a mitral implant. The packaging can be opened in one of two orientations depending upon what is needed and prepares the device to be picked up in the correct orientation. This limits the chance of implanting the heart valve device incorrectly while at the same time reducing the inventory requirements for a medical facility because only one full set of valves needs to be stocked.

Although the present invention has been described in detail, it should be understood that various changes, substitutions and alterations can be made hereto without departing from the spirit and scope of the invention as defined by the appended claims.

What is claimed is:

1. Packaging for a heart valve device, comprising:
a container having an inner compartment, the container having an aortic orientation and a mitral orientation and constructed to be opened in either orientation;
an aortic support member, located in the inner compartment, to support the heart valve device when the container is opened in the aortic orientation such that the heart valve device is prepared for receiving a holding instrument for implantation as an aortic valve; and
a mitral support member, located in the inner compartment, to support the heart valve device when the container is opened in the mitral orientation such that the heart valve device is prepared for receiving a holding instrument for implantation as a mitral valve.

2. The packaging of claim 1, wherein the aortic support member supports the heart valve device with leaflets of the heart valve device held in an open position.

3. The packaging of claim 2, wherein the aortic support member comprises a tab that extends between the leaflets of the heart valve device to hold the leaflets in the open position.

4. The packaging of claim 3, wherein the tab extends from a first ridge that provides central support for the heart valve device, and the aortic support member further comprises a second ridge and a third ridge that provide lateral support for the heart valve device.

5. The packaging of claim 1, wherein the container comprises:
a first container portion having an inner surface defining a first portion of a compartment; and
a second container portion having an inner surface defining a second portion of the compartment;
the first and second container portions formed to removably engage one another.

6. The packaging of claim 5, wherein:
the aortic support member is coupled to the inner surface of the first container portion; and
the mitral support member is coupled to the inner surface of the second container portion.

7. The packaging of claim 6, wherein the aortic support member is formed integral with the first container portion.

8. The packaging of claim 6, wherein the mitral support member is a shelf member removably located inside the second container portion.

9. The packaging of claim 1, further comprising:
an outer shell for housing the container;
the outer shell having a first portion and a second portion formed to engage one another.

10. Packaging for a heart valve device, comprising:
a container having an inner compartment, the container having an aortic orientation and a mitral orientation and constructed to be opened in either orientation, the container comprising:
a first container portion having an inner surface defining a first portion of a compartment; and
a second container portion having an inner surface defining a second portion of the compartment;
the first and second container portions formed to removably engage one another;
an aortic support member located in the inner compartment and coupled to the inner surface of the first container portion, the aortic support member comprising a tab extending into the inner compartment;
the aortic support member supporting the heart valve device, when the container is opened in the aortic orientation, such that the tab holds leaflets of the heart valve device in an open position and such that the heart valve device is prepared for receiving a holding instrument for implantation as an aortic valve; and
a mitral support member located in the inner compartment for supporting the heart valve device when the container is opened in the mitral orientation;

the mitral support member supporting the heart valve device such that the heart valve device is prepared for receiving a holding instrument for implantation as a mitral valve.

11. The packaging of claim 10, wherein the tab extends from a first ridge that provides central support for the heart valve device, and the aortic support member further comprises a second ridge and a third ridge that provide lateral support for the heart valve device.

12. The packaging of claim 10, wherein the aortic support member is formed integral with the first container portion.

13. The packaging of claim 10, wherein the mitral support member is a shelf member removably located inside the second container portion.

14. The packaging of claim 10, further comprising:

an outer shell for housing the container;

the outer shell having a first portion and a second portion formed to engage one another.

* * * * *